(12) United States Patent
Hoftman et al.

(10) Patent No.: US 10,531,931 B1
(45) Date of Patent: Jan. 14, 2020

(54) COMBINATION FLEXIBLE AND SEMI-RIGID LIGHT HANDLE COVER

(71) Applicants: Moshe Hoftman, Calabasas, CA (US); Noel Gharibian, Glendale, CA (US)

(72) Inventors: Moshe Hoftman, Calabasas, CA (US); Noel Gharibian, Glendale, CA (US)

( * ) Notice: Subject to any disclaimer, the term of this patent is extended or adjusted under 35 U.S.C. 154(b) by 302 days.

(21) Appl. No.: 15/476,603

(22) Filed: Mar. 31, 2017

Related U.S. Application Data

(60) Provisional application No. 62/390,536, filed on Apr. 1, 2016.

(51) Int. Cl.
*A45C 13/26* (2006.01)
*A61B 46/10* (2016.01)
(Continued)

(52) U.S. Cl.
CPC .............. *A61B 46/10* (2016.02); *A61B 90/30* (2016.02); *F21V 17/12* (2013.01); *F21V 17/164* (2013.01);
(Continued)

(58) Field of Classification Search
CPC ..... Y10T 16/466; Y10T 16/469; Y10T 16/44; A61B 90/30; A61B 90/36; A61B 90/361; A61B 34/74; A61B 34/76; A61B 46/10; A61B 2017/0046; A61B 2017/00464; A61B 2090/308; B25G 3/04; B25G 3/12;
(Continued)

(56) References Cited

U.S. PATENT DOCUMENTS 4,878,156 A * 10/1989 Hallings ............... F21V 21/403
362/109
4,974,288 A * 12/1990 Reasner ................. A61B 90/36
16/421
(Continued)

OTHER PUBLICATIONS

SemiRigid Handle https://www.xodusmedical.com/Products/18/8/Semi-Rigid-Handle.
(Continued)

*Primary Examiner* — Chuck Y Mah
(74) *Attorney, Agent, or Firm* — Riverside Law LLP

(57) ABSTRACT

The present invention is a combination light handle cover having flexible light handle cover performance in its grip part and semi-rigid light handle performance in its protective upper flange, where two snap fit connections are formed between the invention combination light handle cover and a rigid light handle which is adapted to be fixed rigidly to a surgical light or lamp. A lower snap fit connection is formed between lower female impressions (such as tabs) in the combination light handle cover at a relatively smaller diameter portion of the combination light handle cover in a zone between the grip part and the protective upper flange, which first female impressions snap fit to a lower extension ridge of the rigid light handle. An upper snap fit connection is formed between upper female impressions (such as tabs) in the combination light handle cover at a relatively large diameter portion of the combination light handle cover in a zone upon its protective cover, which second female impressions snap fit to an upper extension ridge of the rigid light handle, which upper extension ridge has a diameter much greater than that of the lower extension ridge.

19 Claims, 13 Drawing Sheets

(51) Int. Cl.
*F21V 33/00* (2006.01)
*F21V 17/16* (2006.01)
*F21V 17/12* (2006.01)
*A61B 90/30* (2016.01)
*F21W 131/20* (2006.01)

(52) U.S. Cl.
CPC .... *F21V 33/0068* (2013.01); *A61B 2090/308* (2016.02); *F21W 2131/20* (2013.01)

(58) Field of Classification Search
CPC ......... B25G 3/24; F21V 17/12; F21V 17/164; F21V 33/0068; F21W 2131/20
See application file for complete search history.

(56) References Cited

U.S. PATENT DOCUMENTS

| | | | | |
|---|---|---|---|---|
| 4,976,299 A * | 12/1990 | Bickelman | ............ | A61B 46/10 150/155 |
| 5,036,446 A * | 7/1991 | Quintanilla | ........... | F21V 21/403 206/223 |
| 5,065,296 A * | 11/1991 | Cude | .................... | F21V 21/403 16/421 |
| 5,355,292 A * | 10/1994 | Hoftman | ............... | F21V 21/403 150/155 |
| 5,469,600 A * | 11/1995 | Sandel | ..................... | B25G 1/02 16/421 |
| 5,709,465 A * | 1/1998 | Lanzone | ............... | F21V 21/406 362/399 |
| 6,370,735 B1 * | 4/2002 | Horan | .................... | A61B 90/36 16/422 |
| 7,757,352 B2 * | 7/2010 | Halamish | ............... | A61B 46/10 16/421 |
| 8,752,987 B1 * | 6/2014 | Hoftman | ............... | A61B 46/10 362/399 |
| 8,763,207 B2 * | 7/2014 | Lawrence | ........... | B29C 45/4407 16/421 |
| 8,789,243 B2 * | 7/2014 | Denmark | ................. | B25G 1/10 16/421 |
| 9,388,971 B2 * | 7/2016 | Lawrence | ........... | B29C 45/4407 |
| 9,480,391 B2 * | 11/2016 | Gharibian | .......... | A61B 1/00142 |

OTHER PUBLICATIONS

Light Handle Covers http://www.medline.com/product/Light-Handle-Covers-By-Cardinal-Health/Z05-PF61065.
Light Handle Covers http://www.medline.com/product/Devon-Disposable-Light-Handles-by-Covidien/Z05-PF27531.

* cited by examiner

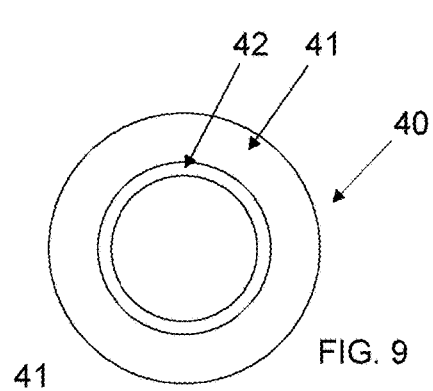
FIG. 9
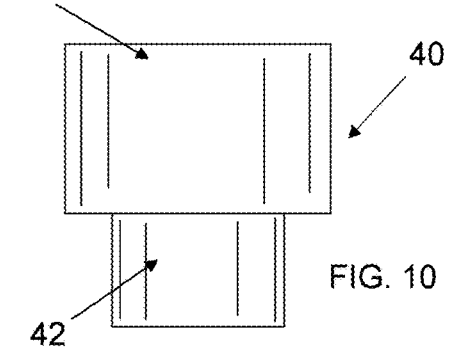
FIG. 10
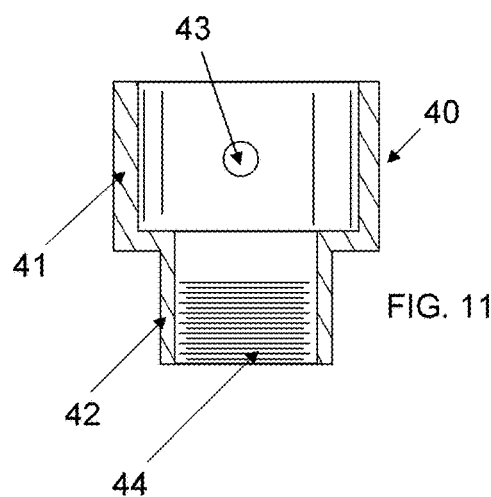
FIG. 11
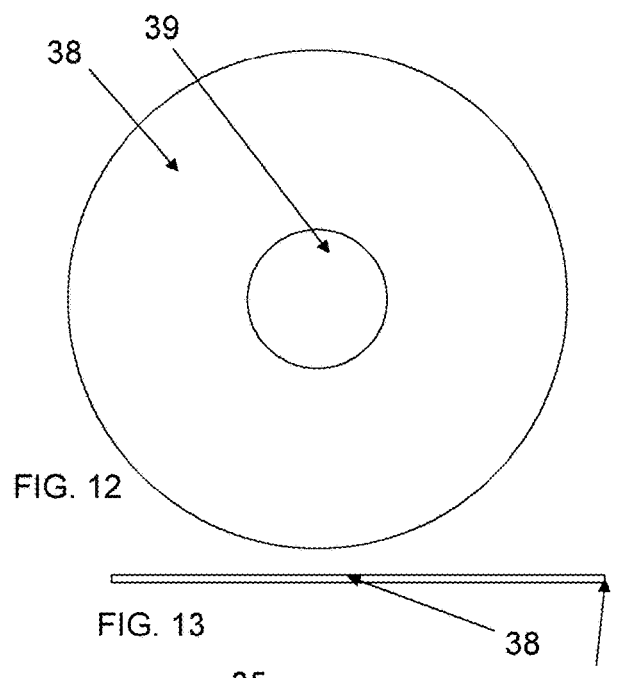
FIG. 12
FIG. 13
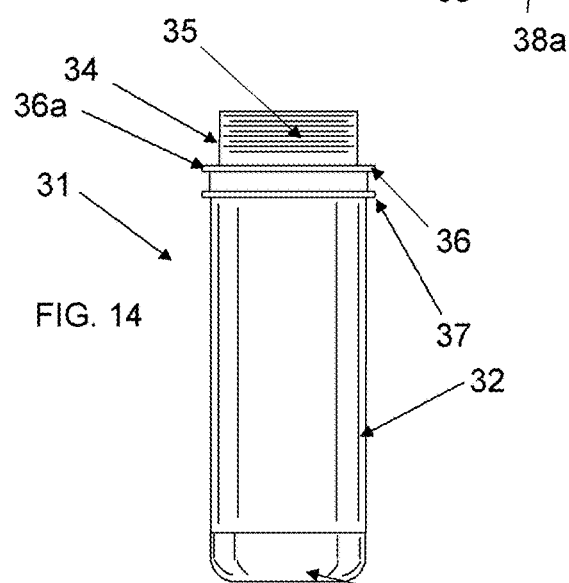
FIG. 14
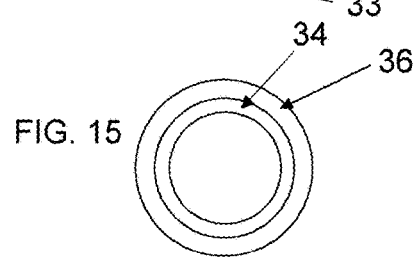
FIG. 15

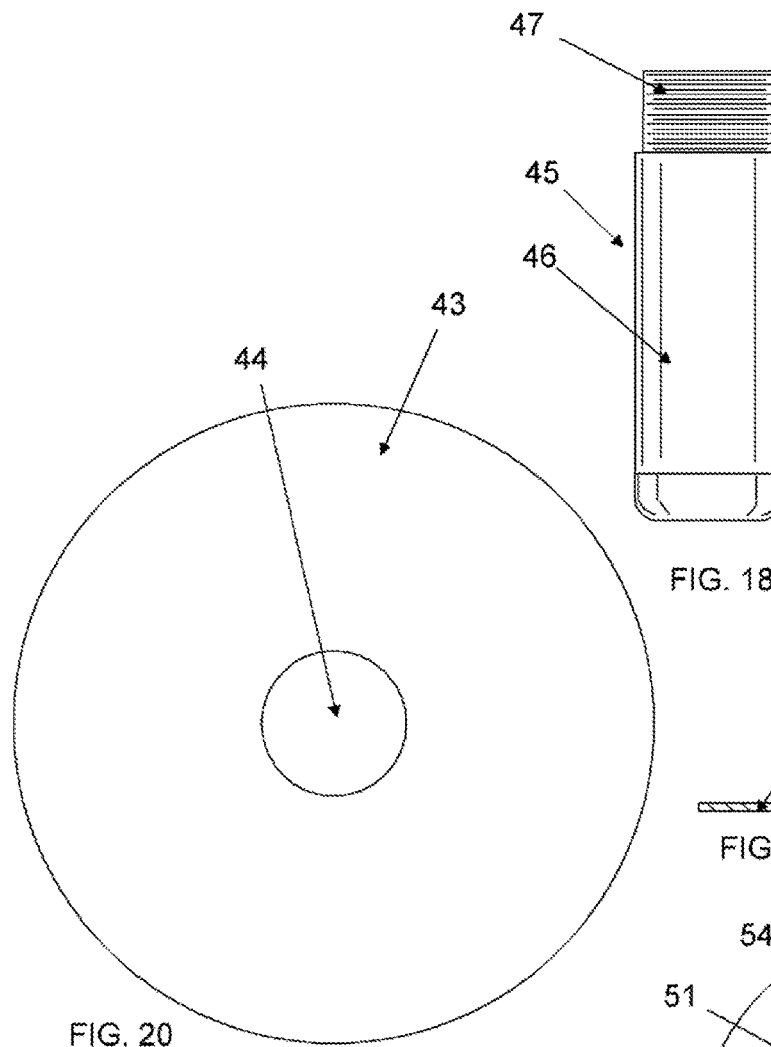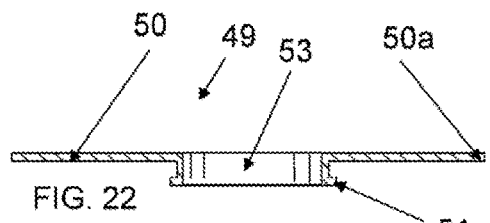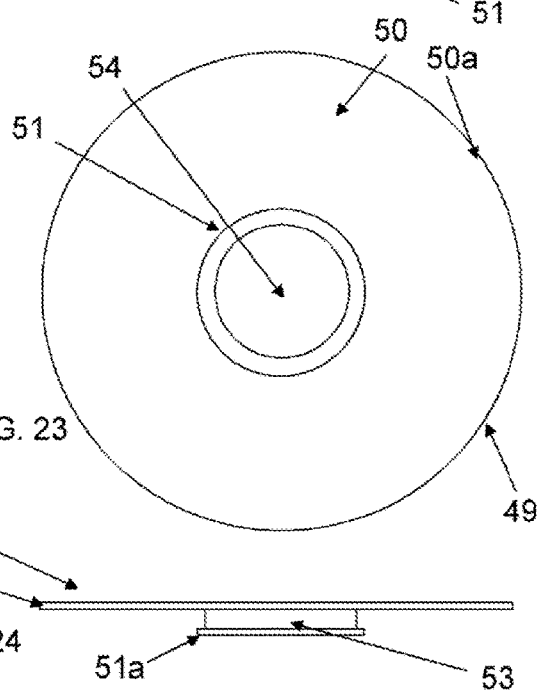

COMBINATION FLEXIBLE AND
SEMI-RIGID LIGHT HANDLE COVER

This application claims priority to U.S. Provisional Patent Application Ser. No. 62/390,536, entitled "Semi-Rigid Light Handle Cover & Light Handle", filed Apr. 1, 2016. The contents of that provisional application are incorporated, in their entirety, by reference herein.

FIELD OF THE INVENTION

The present invention is broadly directed to light handle covers for surgical room lamps which require a continuously sterile surface during the surgical procedure, and more specifically to light handle covers known in the art as semi-rigid light handle covers.

BACKGROUND OF THE INVENTION

Operating room personnel have been aware for years that the repeated touching of the operating room or surgical lamp handle to redirect the illumination pattern or to bring the lamp closer to the area of concern, or to move the lamp farther away, can bring about the spread of contagious diseases through contact with the handle. Such contagious or communicable diseases are borne in or on the human body fluids and tissues which become attached to the exterior surfaces of the gloved (or ungloved) hands of operating personnel, doctors, nurses and other technicians, and are transmitted to the lamp handle or adjusting means through direct contact.

In the environment in which operating room personnel work, i.e. inside the human body, body fluids such as blood and the tissues comprising the organs, muscles and skin of the human body may potentially transmit a number of diseases and viral infections through contact. The process of surgery requires the incision or cutting into the body resulting in the outflow of blood and other body fluids as well as the scattering of various body tissues outside of the point of incision or cut. Some of such fluids and particles of tissues may become attached to the gloved hands of the operating room personnel. Cleaning and sterilization of the lamp handles or adjusting means has remained a serious problem for operating room and other hospital personnel because of their construction and the materials utilized to formulate the handle.

During operating procedures the lamp is almost continually repositioned for better lighting into the point of incision, the interior of the patient's body. The lamp handle is touched by a variety of operating room personnel in attempts to refocus the light onto the desired point of illumination on or in the body of the patient. Refocusing the light emitted by the lamp is accomplished with possibly contaminated exterior surfaces of the gloves worn by the operating room personnel who are still performing the surgical procedure. Anything such personnel may have come into contact with (known or unknown) while their gloved hands were in contact with the human patient will necessarily be transmitted to the surface of the lamp handle or other adjusting means upon touching the surface of such handle or adjusting means.

There have been some attempts to provide covers for surgical lamps for use in a surgical operatory. The phrase "semi-rigid" in the prior art describes a very specific category of surgical light handle covers, as opposed to "flexible" and "rigid".

Semi-rigid surgical light handle covers are described in U.S. Pat. Nos. 4,559,671 and 4,605,124. These patents disclose semi-rigid covers for principally protecting the grip portion of the handle of the surgical lamp, as well as an upward and radially outward extending projection which serves to prevent contact with the handle support elements of the surgical lamp. Other semi-rigid surgical lamp handle covers are disclosed in U.S. Pat. No. 4,844,252 and U.S. D298,864.

Rigid light handle covers are well known in the art as having essentially no ability to be deformed by normal human hand strength, which preclude their storage or manipulation in a space smaller than their undeformed shape. In contrast, "flexible" light handle covers are entirely flexible and are collapsible so as to be folded into a small container, bag or pouch. In contrast, semi-rigid light handle covers of the prior art cannot, without relatively substantial pressure and an appropriately expensive container, be compressed into a small container, bag or pouch, although the structural advantage of the semi-rigid light handle cover over the flexible light handle cover is very substantial, in that application of the semi-rigid light handle cover to the rigid light handle connected to the surgical lamp or light is with low risk of being unable to move the entire piece into fixed connection with the rigid light handle as compared with the "floppy" and non-resistant structure of the flexible light handle cover. The "floppy" nature of the flexible light handle cover provides storage advantage as compared with the semi-rigid light handle cover, but the flexible light handle cover is inherently more risky to use in the surgical suite as opposed to the semi-rigid light handle cover.

However, the current state of the art has shown a substantial disadvantage of the semi-rigid light handle cover, in that its more rigid structure than the flexible light handle cover typically requires more connection force directed toward a longitudinal axis of the rigid light handle in order to obtain the necessary fixation connection. Because surgical lights or lamps must by their very nature be easily movable and positionable with slight force from surgical personnel, said connection force causes displacement of the entire arm of the surgical lamp or light away from the user and resulting in necessarily contaminating an opposite gloved hand of that user to grab the arm of the surgical lamp to force the semi-rigid light handle cover onto fixed connection with the rigid light handle.

There is a need for a light handle cover that combines the advantages of the flexible light handle cover and the semi-rigid light handle cover, which is a present object of the invention.

It is, therefore, an object of the present invention to provide a clean or sterile field around an operating room (surgical) or treatment (clinical) lamp handle or adjusting means in order to alleviate, or entirely eliminate, the task of removal and sterilization of the handles or adjusting means.

It is still a further object of the present invention to provide a barrier or shield which is disposable after a single use and which is easily applied and removed so that the barrier or shield will have greater acceptance among users in the healthcare field.

SUMMARY OF THE INVENTION

The present invention is a combination light handle cover having flexible light handle cover performance in its grip part and semi-rigid light handle performance in its protective upper flange, where two snap fit connections are formed between the invention combination light handle cover and a rigid light handle which is adapted to be fixed rigidly to a surgical light or lamp. A lower snap fit connection is formed between lower female impressions (such as tabs) in the combination light handle cover at a relatively smaller diameter portion of the combination light handle cover in a zone between the grip part and the protective upper flange, which first female impressions snap fit to a lower extension ridge of the rigid light handle. An upper snap fit connection is formed between upper female impressions (such as tabs) in the combination light handle cover at a relatively large diameter portion of the combination light handle cover in a zone upon its protective cover, which second female impressions snap fit to an upper extension ridge of the rigid light handle, which upper extension ridge has a diameter much greater than that of the lower extension ridge.

In a preferred embodiment, the grip part of the combination light handle cover is tapered from the upper female impressions to a lower end of the grip part, with the larger diameter end being always higher in the grip part, so that, in removing the combination light handle cover from a rigid light handle, the grip part of the invention combination light handle cover will tend to invert, with the outer surface of the upper portion of the grip part "peeling down" over the outside surface of the lower portion of the grip part, thereby dramatically and ultimately trapping in an inside-out grip part any contaminants or pathogens which may have undesirably applied to the outside surface of the grip part.

Similarly, but in reverse, if a first combination light handle cover fixed to a rigid light handle is contaminated, it need not be removed in an alternate embodiment of the invention. The tapered grip part of a covering combination light handle cover may be inverted by the user and the inverted grip part applied easily upward onto a contaminated combination light handle cover, whereby at least the lower snap fit connection of the covering combination light handle cover is engaged to the lower extension ridge of the rigid light handle cover, albeit with the lower female impressions of the contaminated combination light handle cover between the covering combination light handle cover and the lower extension ridge of the rigid light handle cover.

The tendency of the protective flange of a flexible light handle cover to be improperly warped, twisted or folded when it is applied to a rigid light handle are eliminated in the invention combination light handle cover. Semi-rigid light handle performance for the protective flange of the invention combination light handle cover is surprisingly obtained with somewhat overlapping material thickness as compared with the prior art flexible light handle cover. The invention combination light handle cover comprises a structure of the protection flange which first rises from the grip part (which includes the lower female impressions) and extends upward and outward to form a circular first structural platform to define a first structural diameter. At the periphery of the first structural platform rises a structural wall for a short distance. At the top of the short structural wall, a second structural platform extends outward and downward to define a second structural diameter at the periphery of the protective flange of the combination light handle cover.

The protection flange structure defines a concave space under side as a result of the first structural plate, structural wall, and second structural plate. Radiating, joined impressions are formed extending across first structural plate, structural wall, and second structural plate. The combination of these structural features provides for the invention combination light handle cover the performance of the semi-rigid light handle cover for the protective cover while, with a relatively thin material thickness overall, the grip part is easily flexed and compressed for flat storage in an storage pouch while preserving the structural integrity of the protective flange (with semi-rigid light handle cover performance) of the invention combination light handle cover. It is an object of the invention to provide a flexible grip part and a semi-rigid protective flange, whereby a lower snap fit connection and upper snap fit connection provide double security for securing the invention combination light handle cover to a rigid light handle having a lower extension ridge and an upper extension ridge.

In the embodiments of the invention, the invention combination light handle cover is adaptable to virtually any type of existing rigid light handle for a surgical light or lamp.

In addition, the present invention comprises an embodiment of a semi-rigid protective flange in a umbrella shape fixed to a grip part that may be rigid, semi-rigid or flexible as those terms refer to light handle covers in the art.

Further, the present invention comprise another embodiment whereby a light handle cover is vacuum formed of a polymer such as polyethylene, polypropylene or the like of a thickness of about 0.025 inches thickness or less to form an upper protective flange which is semi-rigid and a grip part extends down from the protective flange and is sufficiently thinned by the vacuum forming of a relatively small area of the original thickness of the polymer material that the grip part is flexible in the same manner as is known in the art for flexible light handle covers.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF THE DRAWINGS

FIGS. 9, 10 and 11 are respectively bottom, side and side cutaway views of a rigid light handle connector to connect a rigid light handle to a surgical lamp.

FIGS. 12 and 13 are respectively top and side views of an upper connection plate adapted to be affixed to upper tab connectors of the invention combination light handle cover.

FIGS. 14 and 15 are respectively side and top views of a rigid light handle adapted to be fixed to receive the plate of FIG. 12 and be fixed to the connector of FIG. 9.

FIGS. 18 and 19 respectively are side and side cutaway views of a device that is generally representative of rigid light handles available in the prior art and currently, which shows the required function of such a rigid light handle, i.e., to be removably fixed to a surgical lamp at a threaded or similar end, whereby the invention combination light handle cover is shown to be retrofittable to such prior art devices.

FIGS. 20 and 21 are respectively top and side cutaway views of a truncated conical protector which is optionally used with the rigid light handle of FIG. 18.

FIGS. 22, 23 and 24 are respectively side cutaway, bottom and side views of a retrofit adapter for incorporation into a prior art rigid light handle to provide an upper connection plate and a lower connection disk upon which to connect connection tabs of the invention combination light handle cover.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
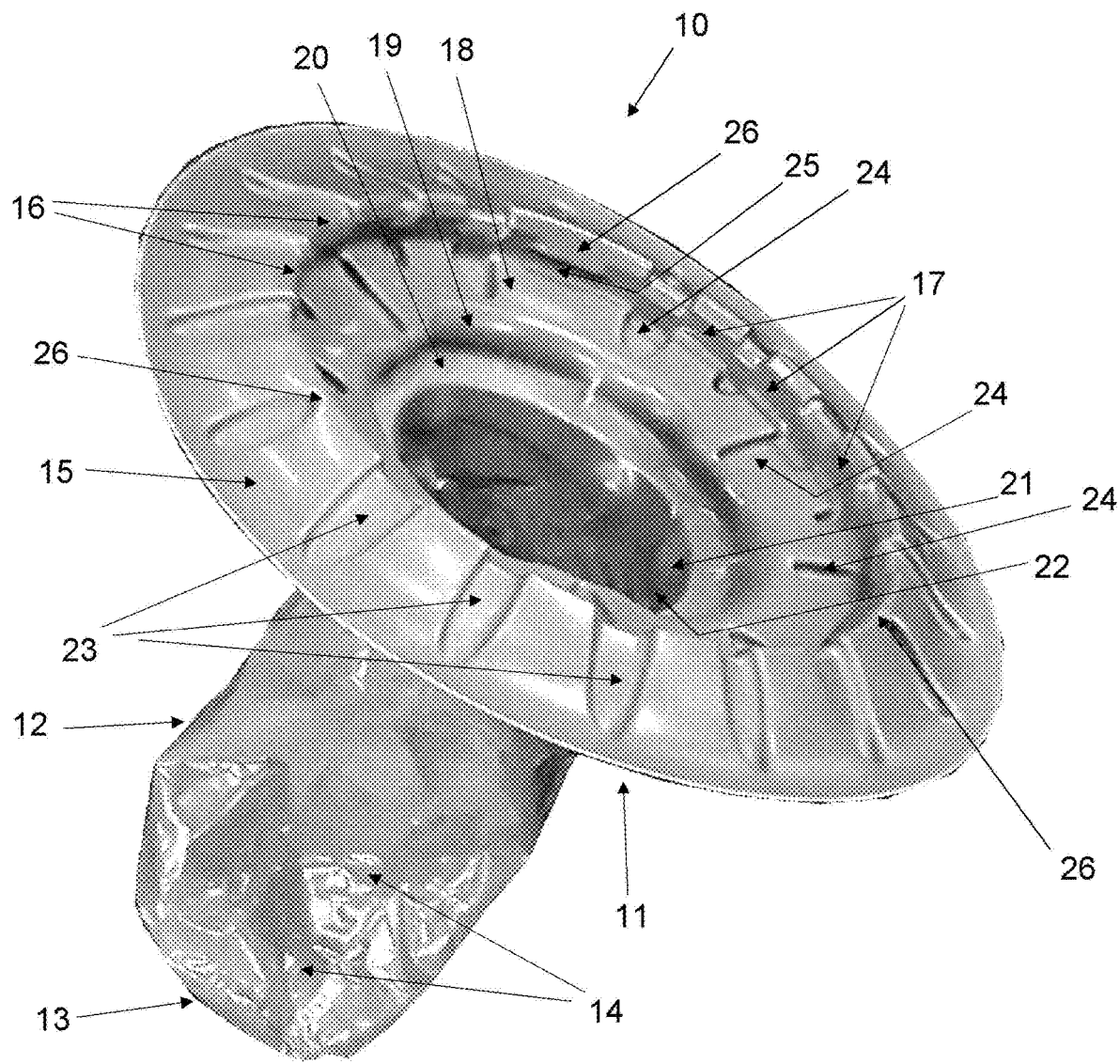
FIG. 1 is a top perspective view of the invention combination light handle cover, showing semi-rigid performance of the protective flange and a flexible grip part similar in performance to that of a flexible light handle cover.

FIG. 1 is a top perspective view of the invention combination light handle cover 10, showing semi-rigid performance of the protective flange 11 and a flexible grip part 12 similar in performance to that of a flexible light handle cover, whereby an extremely strong umbrella shape results from the semi-rigid flange 11. Cover 10 is preferably vacuum formed, a process well known in the art where a flat polymer sheet is heated and vacuumed onto the surface of a metal mold. It is known in the art that semi-rigid light handle covers require at least a polymer thickness of 0.025 inches to achieve a desired rigidity to resist warping, folding and disfigurement typical of the flexible light handle cover, a relatively severe disadvantage in practice, as the protective flange does not form an upward uniform diameter shield. It is a preferred embodiment to vacuum form cover 10 from a starting material of polypropylene sheet of 0.020 inches or less, and even more preferably from a sheet with a thickness of from 0.017 to 0.011 inches, and most preferably from of sheet of about 0.013 inches thick. The present invention surprisingly obtains a semi-rigid performance for flange 11 with a substantially thinner originating polymer sheet than in the prior art by way of a support wall 17 incorporated into the umbrella shape of the flange 11, which support wall 17 is necessary for presentation of three upper connection tabs 26, each having undercuts 25. Upper connection tabs 26 preferably extend over the undercuts 25 and inward from wall 17 by from 1 to 3 millimeters.

The general umbrella shape of flange 11 is provided by peripheral upward rising plate 15 (preferably about 0.5 to 1.0 inches in width), which rises to a maximum elevation at crest 16, from which support wall 17 (preferably from 0.125 to 0.5 inches in height, most preferably 0.25 inches in height) descends to an inner descending round plate 18, which extends structurally to a top opening of grip part 12, transitioning through wall 19 and round plate 20. It is preferred that upper impressions 23 into the upper surface of plate 15 extend structurally integral with lower impressions 24 into the upper surface of plate 18 to provide additional resistance to torsion and flexion forces that may be applied to the flange 11, although the objects of the invention may be obtained by way of the umbrella shape provided by plate 15, wall 17, and plate 18 without as many impressions 23 and 24 or, in one embodiment, no such impressions as are shown in the drawing figures and described herein. Impressions 23 and 24 are generally oval in shape with a depth preferably of from 2 to 5 millimeters, with a top portion of the oval shape in impression 23 and a lower portion of the oval shape in impression 24, with no impression made into wall 17. Flange 11 has a peripheral round shape overall to act as a shield on its underside during use. Grip part 12 comprises a very flexible wall 14, preferably from about 0.002 to 0.080 in thickness, a bottom 13, and an upper portion extending down from plate 20, whereupon are lower connection tabs 21 that have undercuts 22, and lower connection tabs extend inward from the upper portion wall of grip part 12 by 1 to 4 millimeters.

Upper connection tabs 26 and lower connection tabs 21 are critical to the objects of the invention, in that two or more such tabs must be located respectively upon support wall 17 and upon the upper portion wall of grip part 12 to engage, respectively, with a large disk and a small disk to form the invention upper tab connection and lower tab connection by which cover 10 is affixed to a rigid light handle and provides secure and sterile protection to a user from the underlying surfaces. It is another object of the invention that cover 10 is adapted to have a first cover 10 affixed to a rigid light handle and a second cover 10 is easily slipped over the outer surface of the first cover 10 and thereby also securely affixed to the rigid light handle.

Figure 2:
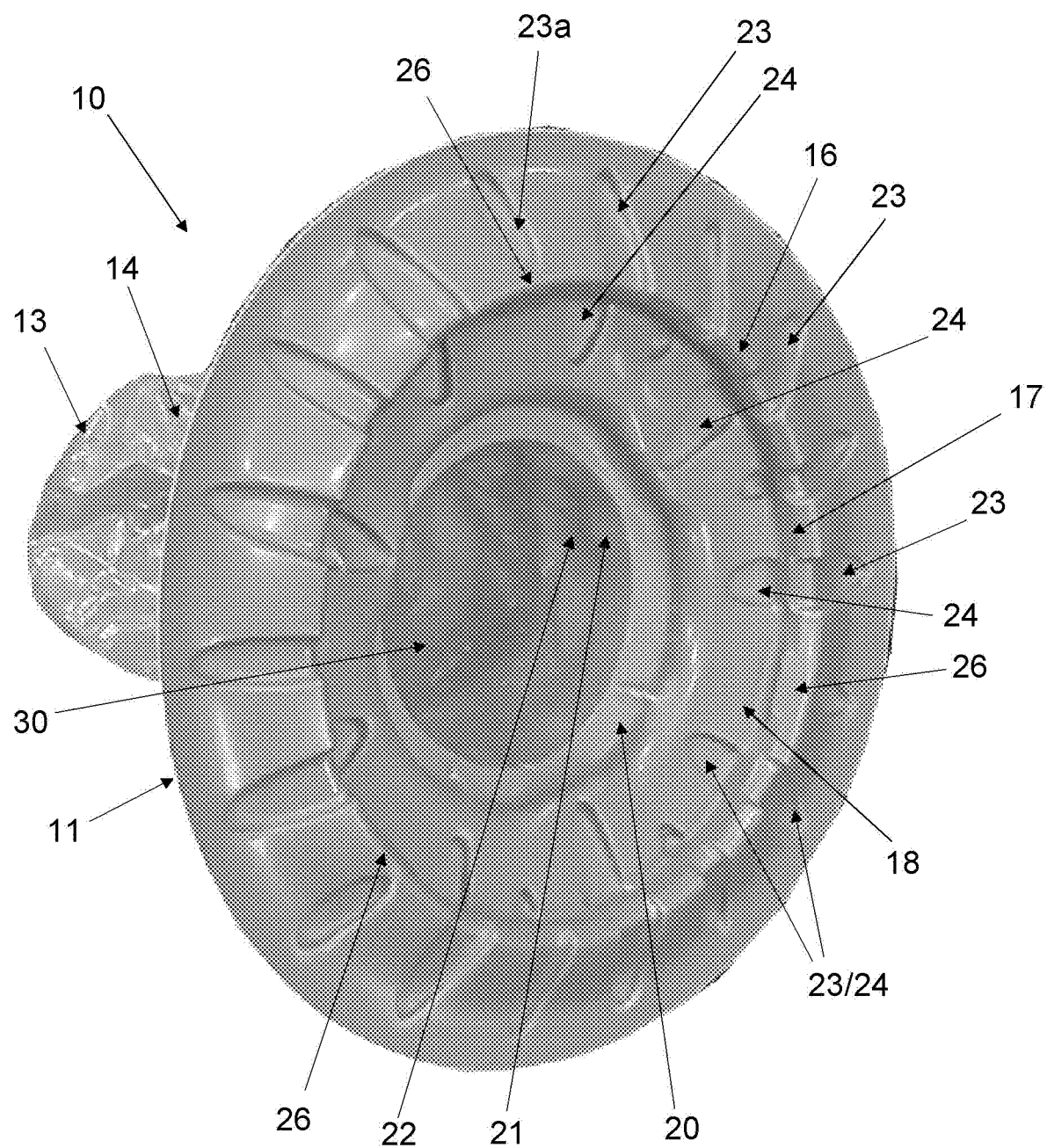
FIG. 2 is a slightly different top perspective view of the invention combination light handle cover, showing semi-rigid performance of the protective flange and a flexible grip part similar in performance to that of a flexible light handle cover.

FIG. 2 is a slightly different top perspective view of the invention combination light handle cover 10, showing semi-rigid performance of the protective flange 11 and a flexible grip part 12 similar in performance to that of a flexible light handle cover, where impressions 23a are formed in plate 15 to enhance support of upper connection tabs 26.

Figure 3:
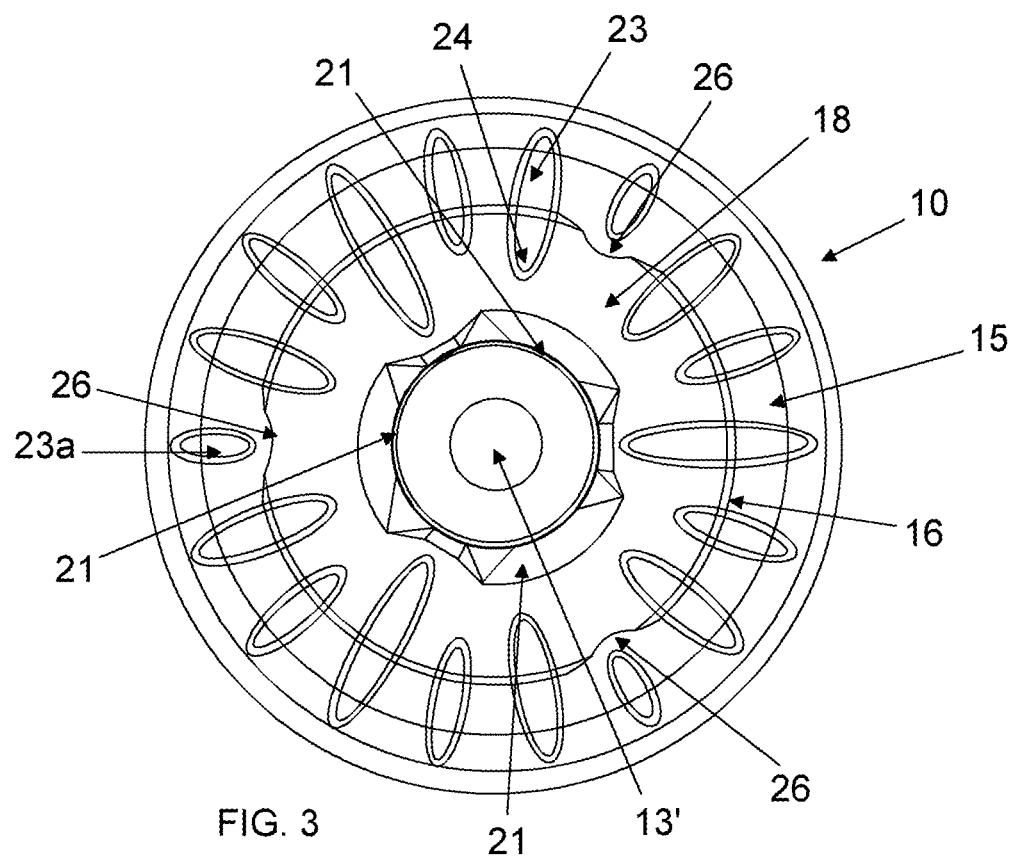
FIG. 3 is top view of the combination light handle cover shown in FIG. 1.
Figure 4:
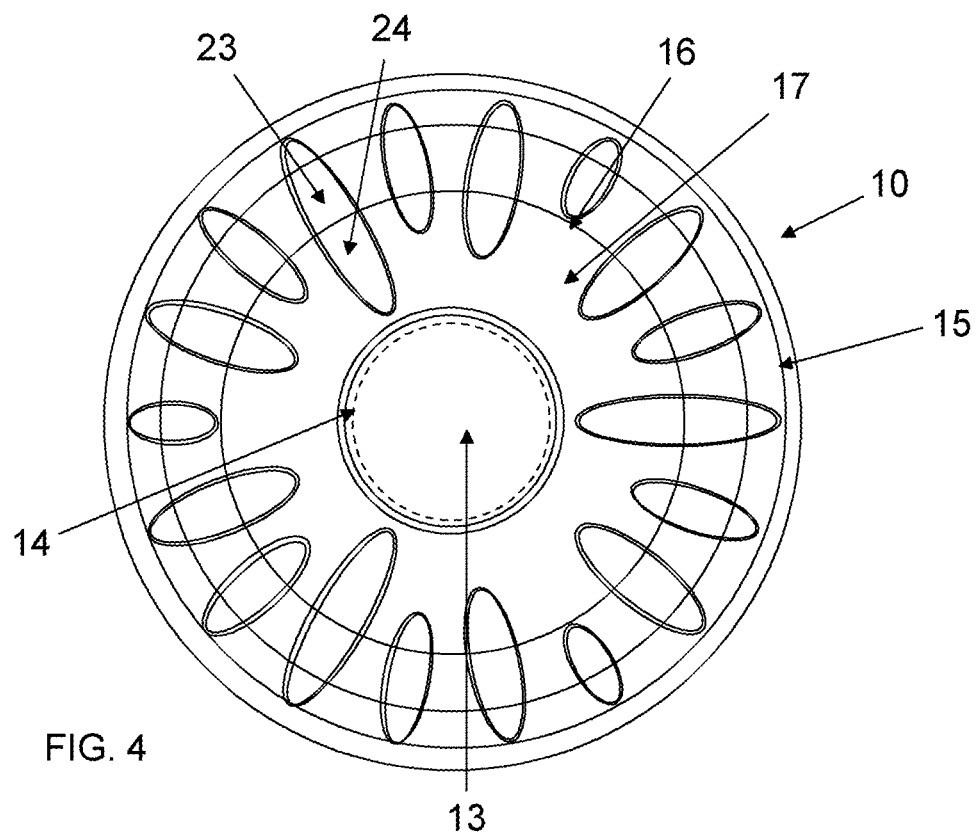
FIG. 4 is a bottom view of the combination light handle cover shown in FIG. 1.

FIG. 3 is top view of the combination light handle cover 10 shown in FIG. 1 and FIG. 4 is a bottom view of the combination light handle cover 10 shown in FIG. 1, whereby an opening 13' is shown in bottom 13 to provide for a camera incorporated into a rigid light handle and having its lens directed through opening 13'.

Figure 5:
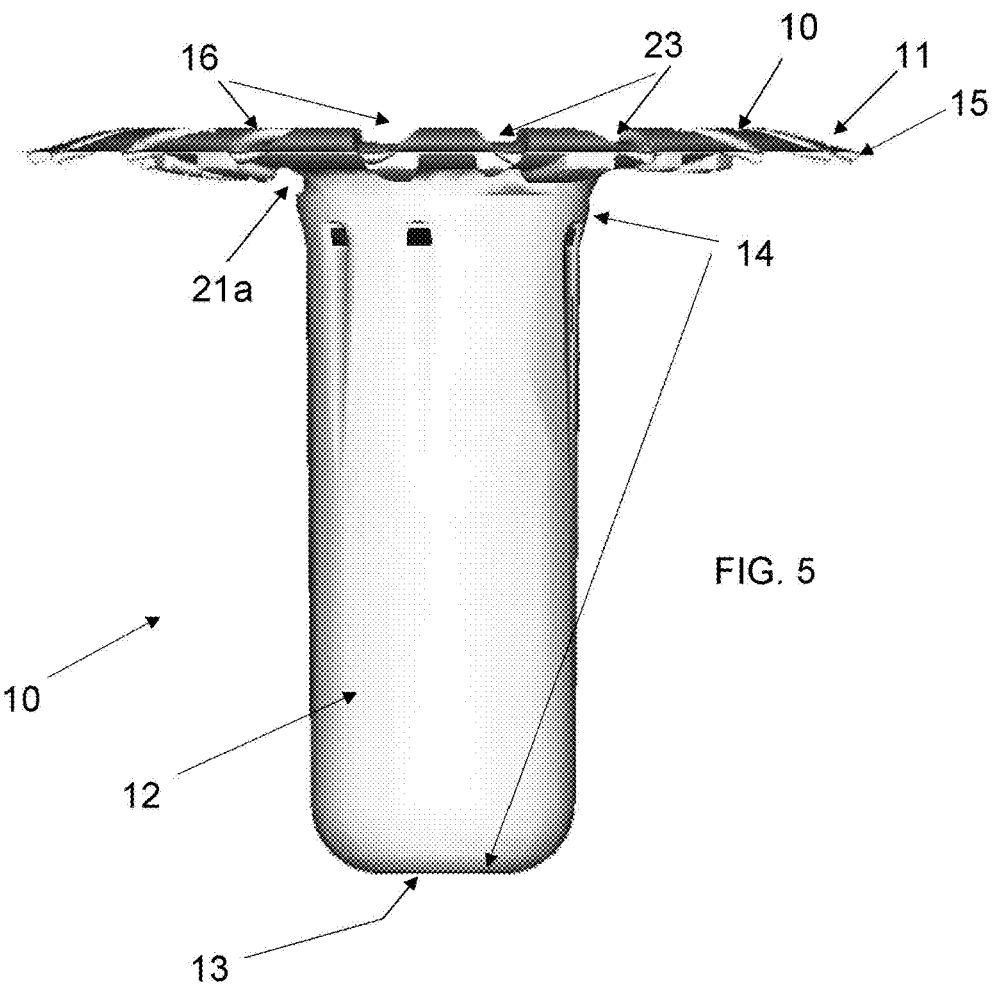
FIG. 5 is a side view of the combination light handle cover shown in FIG. 1.
Figure 6:
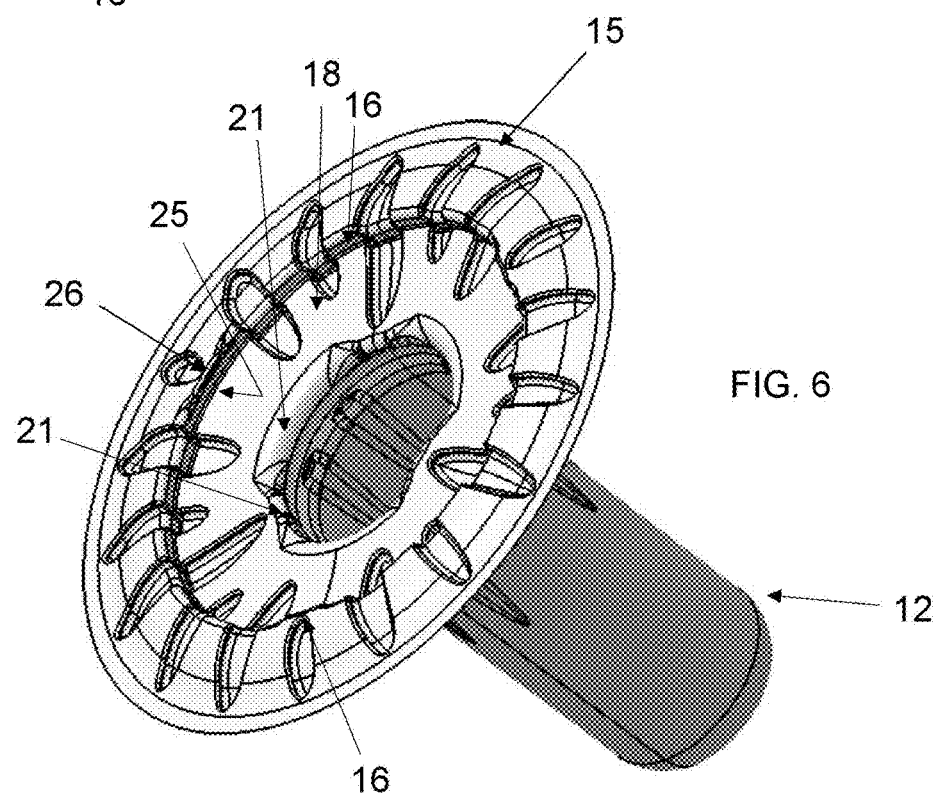
FIG. 6 is a top perspective view of the invention combination light handle cover, showing semi-rigid performance of the protective flange and an expanded flexible grip part.
Figure 7:
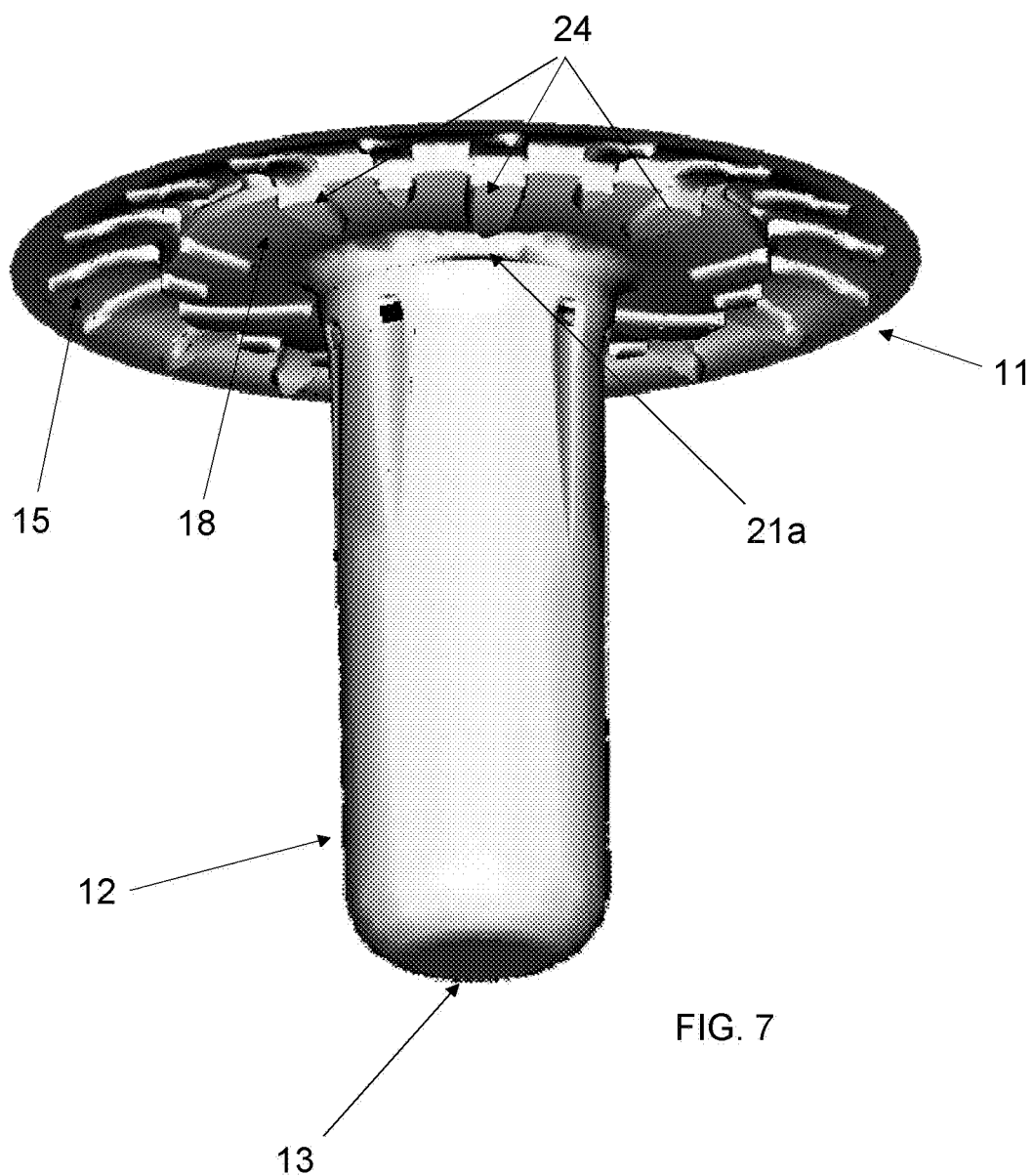
FIG. 7 is a bottom perspective view of the invention combination light handle cover, showing semi-rigid performance of the protective flange and an expanded flexible grip part.
Figure 8:
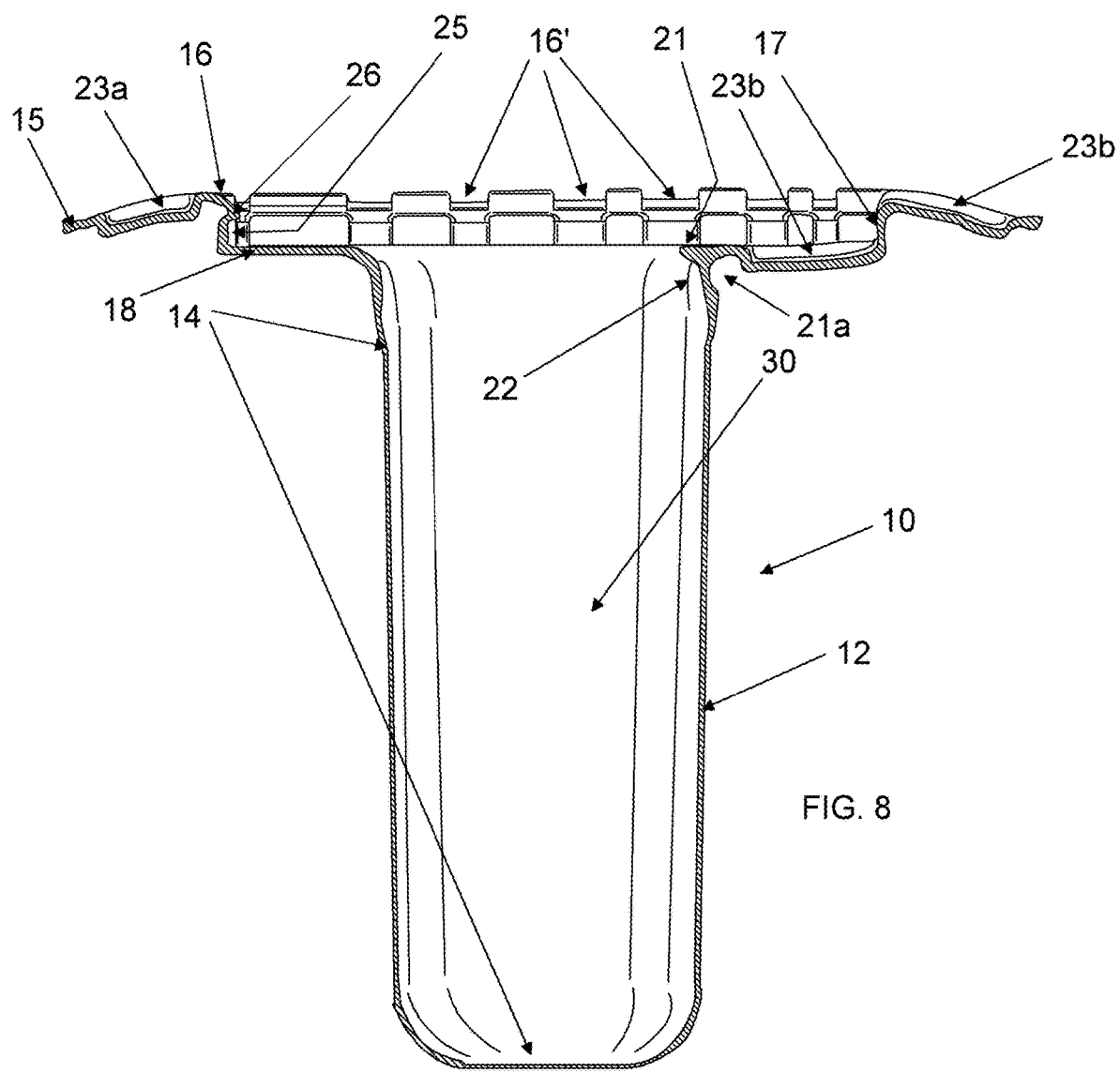
FIG. 8 is a cross section view of the combination light handle cover shown in FIG. 5.

FIG. 5 is a side view of the combination light handle cover 10 shown in FIG. 1, showing that three impressions 21a are formed into the outside of an upper portion of grip part 12, impressions 21a each thereby, by way of the vacuum forming step, resulting in the inward extending and molded lower connection tabs 21. Said impressions 21a are an essential feature of the ability of cover 10 to receive and fix upon its lower outer surface another cover 10, where said impressions 21a are adapted to receive lower connection tabs 21 of a second cover 10, as described below. FIG. 6 is a further top perspective view of the invention combination light handle cover 10, showing semi-rigid performance of the protective flange and an cylindrical grip part 12. FIG. 7 is a bottom perspective view of the invention combination light handle cover, showing semi-rigid performance of the protective flange 11 and an expanded cylindrical flexible grip part 12. FIG. 8 is a cross section view of the combination light handle cover 10 shown in FIG. 5, with a space 30 defined in the walls 14 of grip part 12 and impressions 23b extending from plate 15 to plate 18 in a preferred structural support of tabs 21.

FIGS. 9, 10 and 11 are respectively bottom, side and side cutaway views of a rigid light handle adapter connector 40 to connect a rigid light handle to a surgical lamp. An upper cylindrical section 41 comprises a relatively large internal space with hole 43, which is adapted to be fixed to a standard surgical lamp for further attachment of rigid light handles such as in FIGS. 14 and 15 and 18 and 19. Connector 40 has a lower cylindrical section 42 with internal threaded section 44.

FIGS. 12 and 13 are respectively top and side views of an upper connection plate 38 adapted to be affixed to upper connection tabs of the invention combination light handle cover, where a hole 39 is defined in plate 38. The outer edges of plate 38 are upper connection contacts 38a which are received in the undercuts 25 of the cover 10 of FIG. 8 and which are also impressed upon support wall 17 of FIG. 8 when plate 38 is engaged with cover 10 to form the upper connection.

FIGS. 14 and 15 are respectively side and top views of a rigid light handle 31 adapted to be fixed to receive the plate 38 of FIG. 12 and be fixed to the connector 40 of FIG. 9. Handle 31 comprises a generally hollow cylindrical piece with an open top with a rigid, usually metal grasp portion 32, which can be polygonal or round in horizontal cross section and can have surface grooves or irregularities to enhance the ability of the user of guide a surgical lamp by grasping portion 32. An upper connection part 34 has an outer threaded section 35, which adapted to be threadedly connected with the inside threads of the inside threaded section 44 of connector 40 of FIG. 11. Disks 36 and 37 extend outward from a portion of handle 31 above grasping portion 32 and below upper part 34, providing at the edges of disk 36 the lower connection contacts 36a, which are adapted to cause lower connection tabs 21 of FIG. 8 to be fixed immediately beneath them when cover 10 is fixed to handle 31. The portion of handle 31 between upper part 34 and grasping portion 32 may be integrally formed with handle 31 or may be a separate piece with a center opening that can slide over upper part 34 and be secured to a top edge of grasping portion 32.

Figure 16:
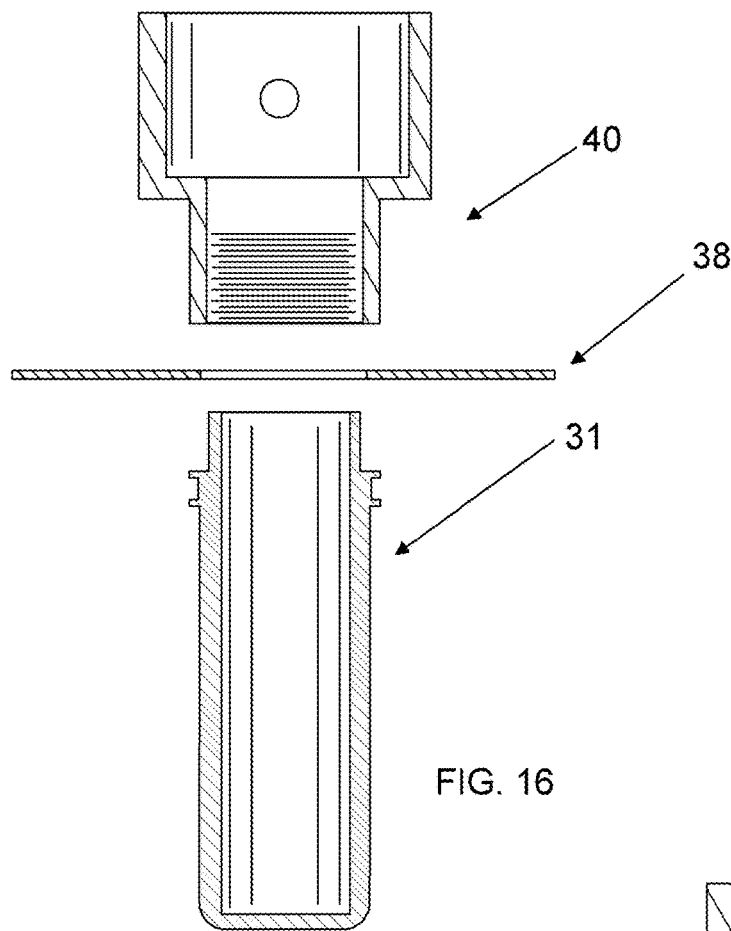
FIG. 16 is a side cutaway and exploded view of the rigid light handle of FIG. 15, the plate of FIG. 12 and the connector of FIG. 9.

FIG. 16 is a side cutaway and exploded view of the rigid light handle 31 of FIG. 15, the plate 38 of FIG. 12 and the connector 40 of FIG. 9.

Figure 17:
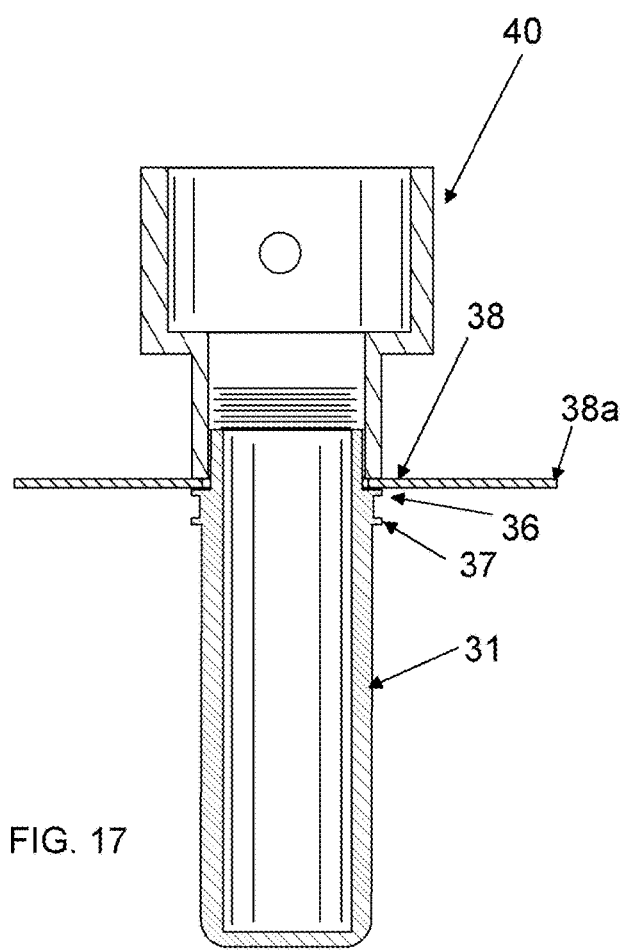
FIG. 17 is a side cutaway and assembled view of the rigid light handle of FIG. 15, the plate of FIG. 12 and the connector of FIG. 9.

FIG. 17 is a side cutaway and assembled view of the rigid light handle 31 of FIG. 15, the plate 38 of FIG. 12 and the connector 40 of FIG. 9, where upper connection contacts 38a and lower connection contacts 36a are fixed rigidly and horizontally in place as plate 38 is fixed securely in horizontal position between the threaded connection of connector 40 to handle 31. The assembly shown in FIG. 17 is ready to receive and fix to handle 31 and plate 38 the invention cover 10.

FIGS. 18 and 19 respectively are side and side cutaway views of a device handle 45 that is generally representative of rigid light handles available in the prior art and currently, which shows the required function of such a rigid light handle 45, i.e., to be removably fixed to a surgical lamp at a threaded or similar end, whereby the invention combination light handle cover 10 is shown to be retrofittable to such prior art devices. Handle 45 comprises a hollow cylindrical body with a top threaded section 47 and a lower grasping portion 46. Optional for use with handle 45 is, as shown in FIGS. 20 and 21, a truncated conical protector 43 with center opening 44.

FIGS. 22, 23 and 24 are respectively side cutaway, bottom and side views of a retrofit adapter 49 for incorporation into a prior art rigid light handle to provide an upper connection plate and a lower connection disk upon which to respectively to connect upper and lower connection tabs of the invention combination light handle cover. Adapter 49 comprises an upper connection plate 50 with upper connection contacts 50a (which serve the same purpose as upper connection contacts 38a of FIG. 17) and a lower connection disk 51 with lower connection contacts 51a (which serve the same purpose as the lower connection contacts 36a of FIG. 17). Spacer section 53 separates plate 50 from disk 51. Opening 54 is adapted to allow adapter 49 to be slipped onto section 47 of handle 45 of FIG. 45 and to be held in place by connector 40, as similarly shown in FIG. 17.

Figure 25:
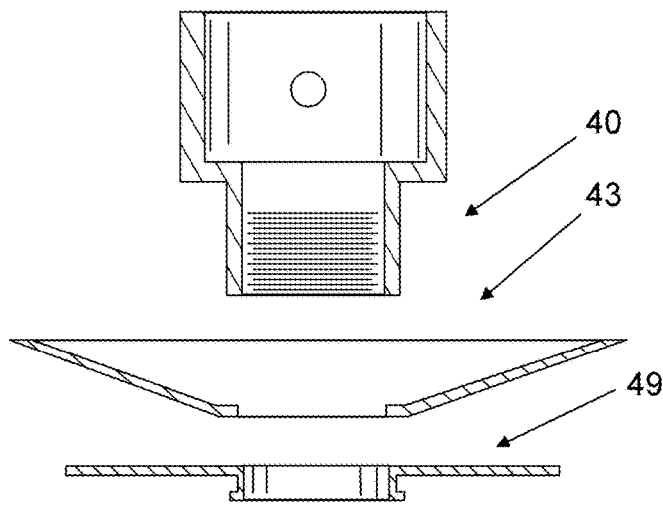
FIG. 25 is a side cutaway and exploded view of the rigid light handle of FIG. 18, the adapter of FIG. 24, the conical protector of FIG. 20, and the connector of FIG. 9.
Figure 26:
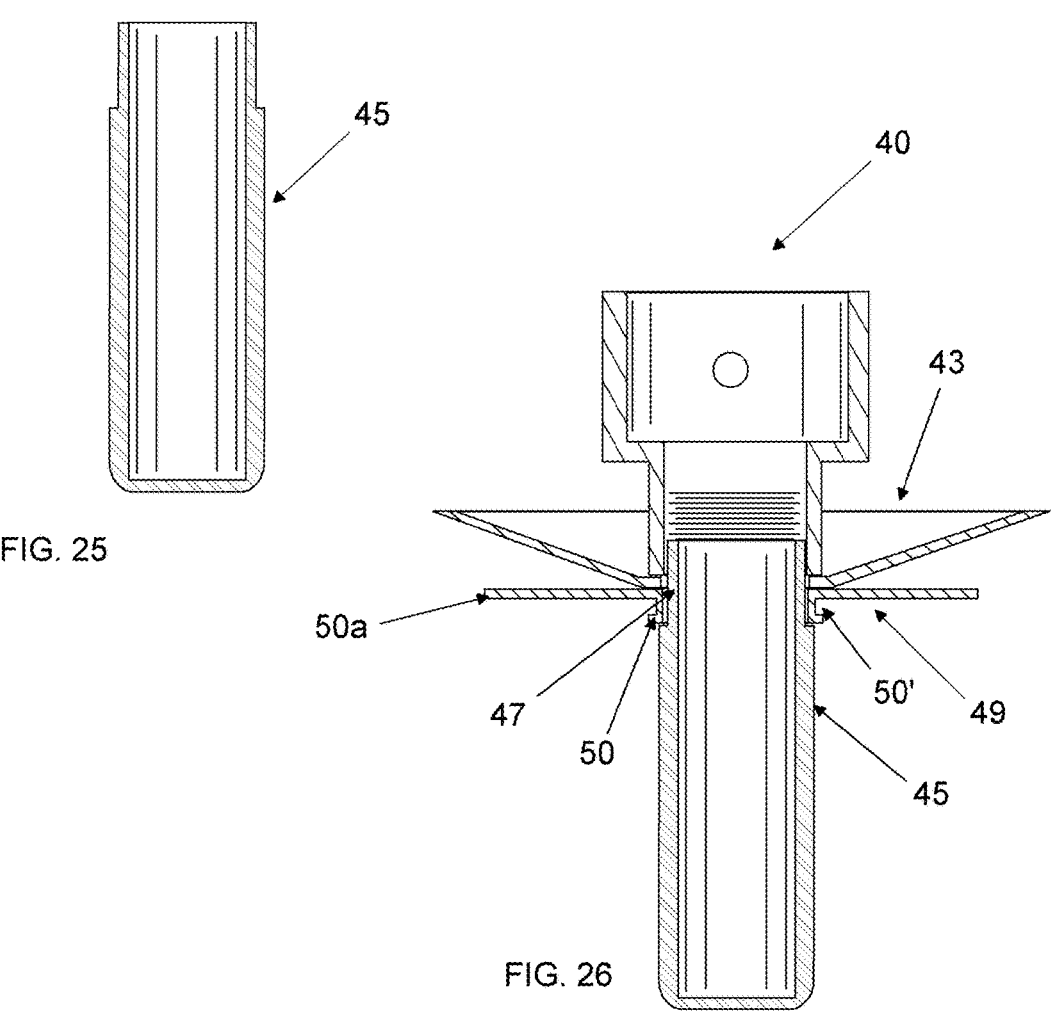
FIG. 26 is a side cutaway and assembled view of the rigid light handle of FIG. 18, the adapter of FIG. 24, the conical protector of FIG. 20, and the connector of FIG. 9.

FIG. 25 is a side cutaway and exploded view of the rigid light handle 45 of FIG. 18, the adapter 49 of FIG. 24, the conical protector 43 of FIG. 20, and the connector 40 of FIG. 9. FIG. 26 is a side cutaway and assembled view of the rigid light handle 45 of FIG. 18, the adapter 49 of FIG. 24, the conical protector 43 of FIG. 20, and the connector 40 of FIG. 9, resulting in horizontal and rigid presentation of upper connection contacts 50a and lower connection contacts 51a, accomplishing in retrofit with adapter 49 for a prior art rigid light handle the necessary connection contacts for the invention as those for another embodiment for handle 31 if FIG. 17, where lower connection contacts 36a are optionally integral with handle 31.

Figure 27:
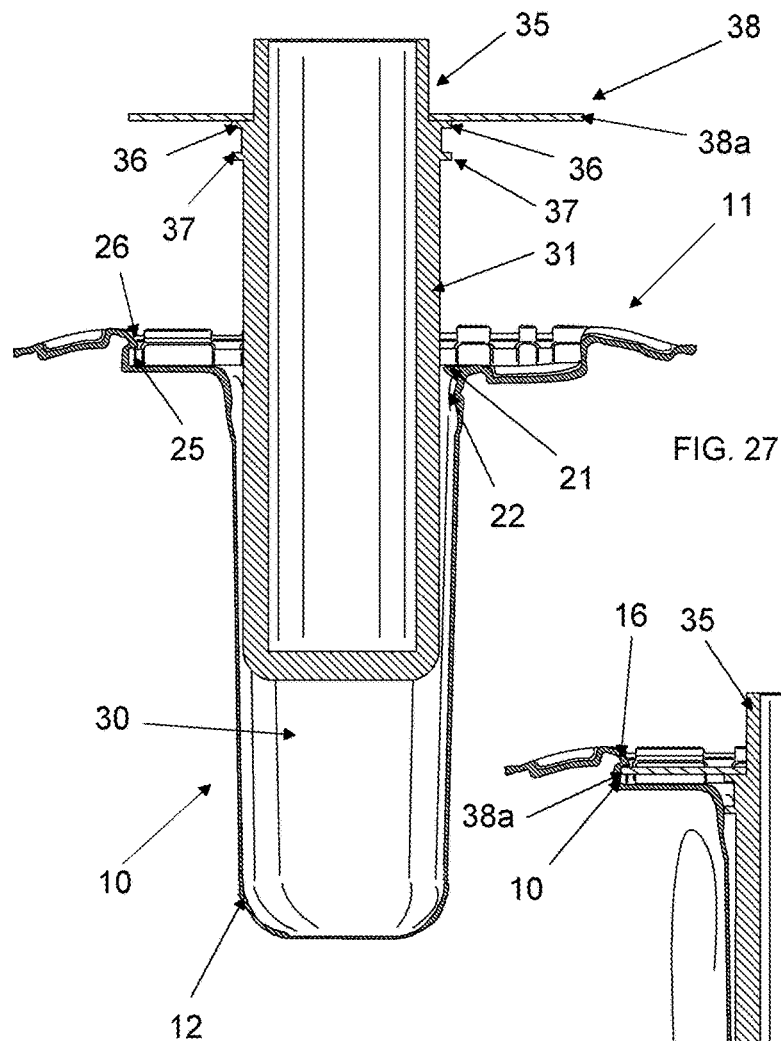
FIG. 27 is the combination light handle cover of FIG. 8 shown being inserted onto the rigid light handle of FIG. 17.

FIG. 27 is the combination light handle cover 10 of FIG. 8 shown being inserted onto the rigid light handle 31 of FIG. 17, showing plate 38 held horizontally and rigidly in place, the combination thereby presenting horizontally connection contacts 38a and 36a and grasping portion 32 (FIG. 14) being inserted into the space 30 within the flexible walls 14 of grip part 12. Flange 11 has an upper surface being moved upwardly in the direction of disk 36 and an underside of plate 38, whereby, respectively, lower connection tabs 21 shall be captured between disks 36 and 37 and upper connection undercuts 25 shall capture upper connection contacts 38a under upper connection tabs 36.

Figure 28:
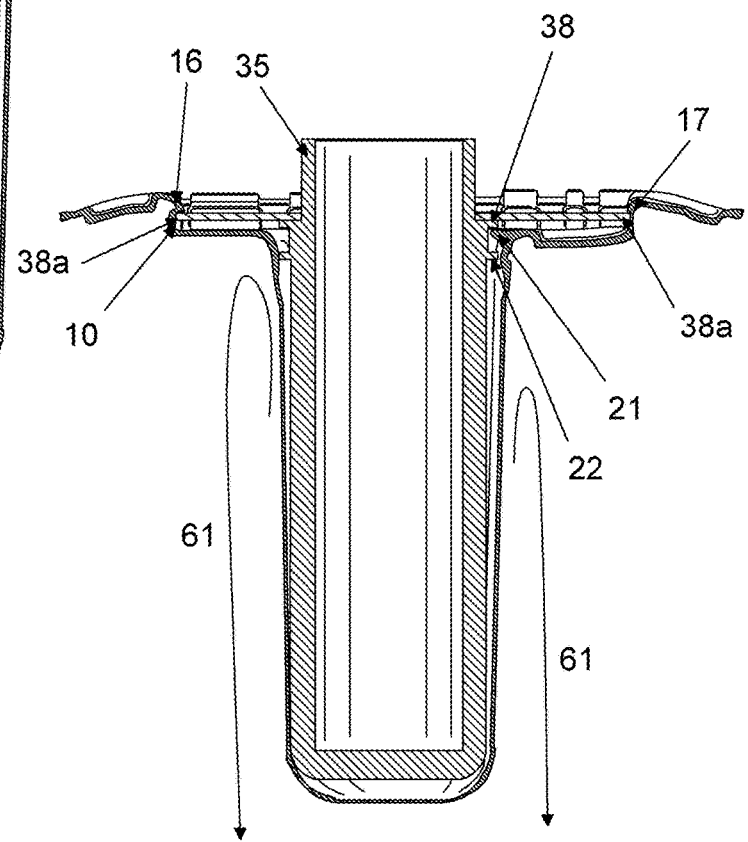
FIG. 28 is the combination light handle cover of FIG. 8 shown fully connected at upper and lower connection tabs onto the rigid light handle of FIG. 17 and showing the "peel down" removal of the grip part.

FIG. 28 is the combination light handle cover 10 of FIG. 8 shown fully connected at upper and lower connection tabs onto the rigid light handle 31 and plate 38. It is understood that upper connection tabs 26 and undercuts 25 may be arranged with as few as two such tabs and undercuts on wall 17, but three or more are preferred for better fixing of plate 38 to a top surface of flange 11. It is also understood that lower connection tabs 21, as captured between disks 36 and 37, be arranged with as few as two such tabs on an upper portion of an inside surface of the grip part 12, but three or more are preferred for better fixing of the top of the grip part 12 to the handle 31.

It is a preferred embodiment of the cover 10 that grip part 12 comprise a substantially tapered vertical cross section, with a wider diameter at the top of the grip part 12 than at bottom 13 thereof. FIG. 28 shows the path 61 in which grip part 12 will invert and turn inside out where such tapering, with a lower section of grip part 12 having an inside diameter close to an outer diameter of the grasping portion 32 of handle 31. The inversion of grip part 12 will occur as a result of its highly flexible nature and frictional contact between an inside surface of a lower section of grip part 12 and an outside surface of grasping portion 32 of handle 31 when cover 10 is disengaged from connection contacts 38a and from between disks 36 and 37 and pulled downward. Said inversion will result in desirable capture of contaminants on the outside surface of grip part 14 within a downward cavity formed by inversion of grip part 12.

Figure 29:
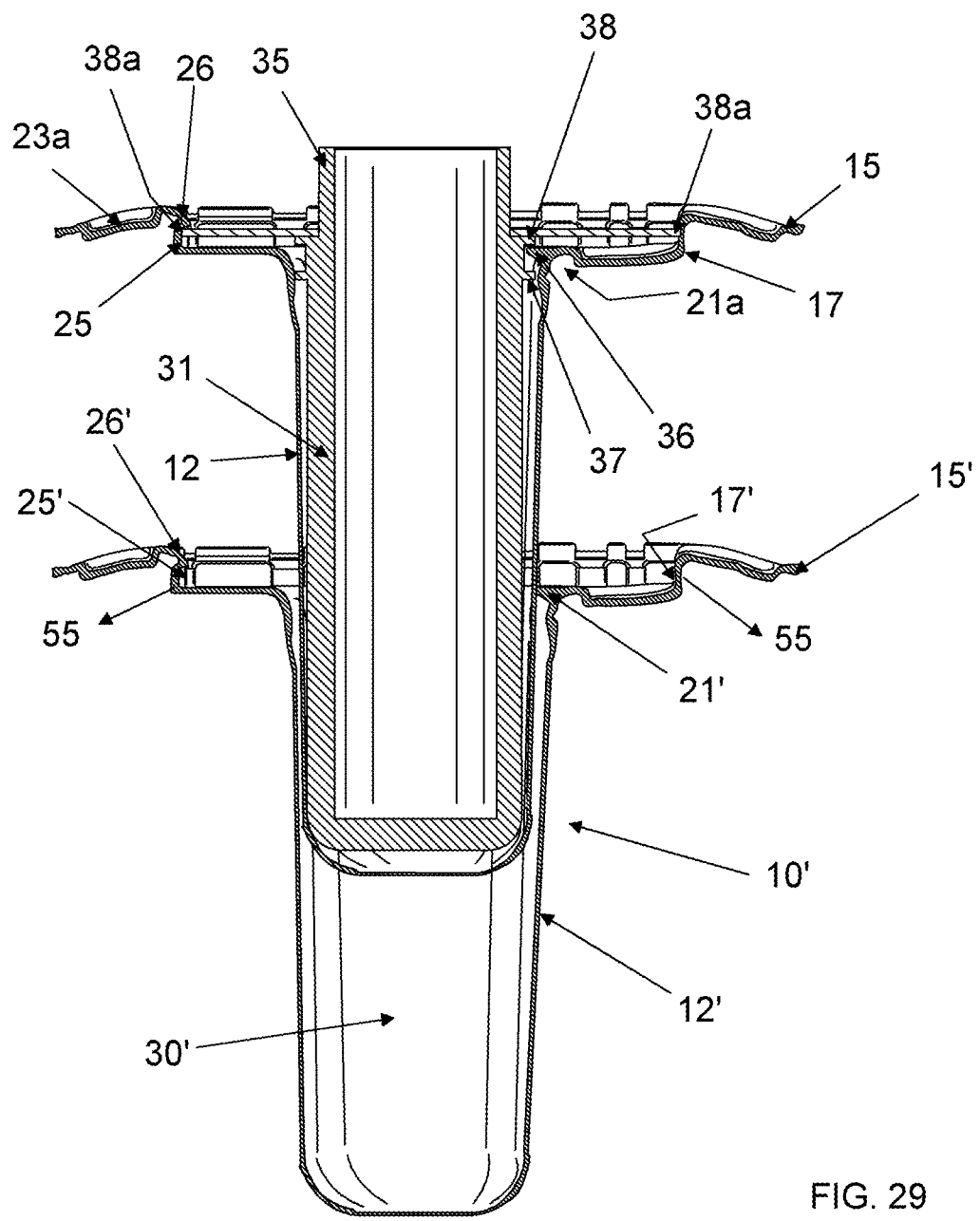
FIG. 29 is a first combination light handle cover and rigid light handle of FIG. 28 with a second combination light handle cover being moved into position to cover the entire underside of the first combination light handle cover.

FIG. 29 is a first combination light handle cover 10 and rigid light handle of FIG. 28 with a second combination light handle cover 10' being moved into position to cover the entire underside of the first combination light handle cover 10. Lower connection tabs 21' of cover 10' are adapted to snap fit into lower connection recesses 21a of cover 10 and wall 17' of cover 10' is adapted to expand or bend slightly in directions 55 radially outward to cause flange 11' to be fixed and engaged to plate 38 with flange 11 of cover 10 in between them.

Figure 30:
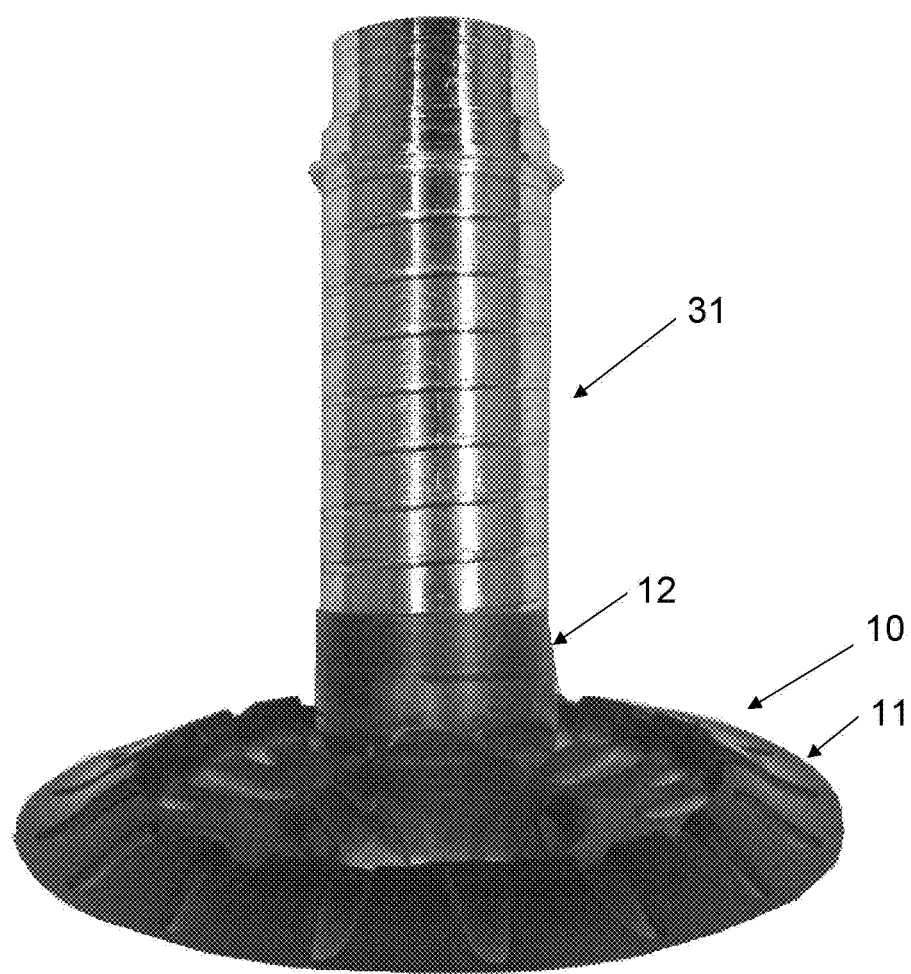
FIG. 30 shows the result of causing the invention combination light handle cover to be removed from the rigid light handle.

FIG. 30 shows the result of causing the cover 10 to be removed from the rigid light handle 31 as described for FIG. 29 and paths 61, wherein grip part 12 inverts and causing the original inside surface to become an outside surface.

In a further description of the present invention, a semi-rigid polymer about 0.010 to 0.015 inches is vacuum formed and adapted to be fixed on a rigid light handle, as described above. As compared with prior art semi-rigid light handle cover using material so at least 0.025" thickness, the present invention reduces polymer usage for the function of semi-rigid light handle covers by as much as 40 percent. In a preferred embodiment, the rigid light handle of FIGS. 14 and 18 comprise a horizontal diameter larger by 5-15 percent at a bottom section than at a top section for surgeon comfort.

It is an important embodiment of the invention to provide that the lower end of the grasping portion of the rigid light handle is from 0.125 to 0.750 inches greater in a first horizontal diameter than a second horizontal diameter of the greater part of said grasping portion and the grip part has an internal diameter of from slightly less than the first horizontal diameter to slightly greater than the second horizontal diameter to accomplish the effect as shown in FIG. 30.

It has been described above that the protective flange has an umbrella shape comprising a round rising plate, a support plate extending down from a crest and facing inward to a center of the protective flange, and a descending round plate to achieve a semi-rigid performance of the protective flange. It is a flattened embodiment of the invention light handle cover to provide for a different structure for the protective flange, in that the round rising plate and the descending round plate will be horizontal relative to a central axis of the invention light handle cover, resulting in, respectively, an outer flat plate and an inner flat plate with an intervening support wall facing inward and extending up from an outer edge of the inner flat plate to provide for a presentation surface for the upper connection tabs. This arrangement will result in either (1) the outer flat plate will be at a different elevation than the inner flat plate or (2) the outer flat plate will extend from a bottom edge of the support wall allowing for the first flat plate and the second flat plate to be at the same elevation.

It is to be understood that while certain forms of the present invention have been illustrated and described herein, it is not to be limited to the specific forms or arrangement of parts described and shown.

What is claimed is:

1. An assembly of a rigid light handle for a maneuverable surgical lamp and light handle cover comprising:
   (a) the rigid light handle comprising a generally cylindrical grasping portion with a handle connector extending upward from the grasping portion and adapted to be connected with the maneuverable surgical lamp, whereby the grasping portion defines a vertical axis;
   (b) a round upper connection plate with an outer edge defining an upper connection contact, the upper connection plate being fixed rigidly and horizontally about the vertical axis to the rigid light handle above the grasping portion but below a top end of the handle connector;
   (c) a lower round connection disk fixed rigidly about the vertical axis and above the grasping portion but below and spaced apart from an underside of the upper connection plate, thereby defining a lower connection space, and whereby a diameter of the round upper connection plate is substantially greater than a diameter of the lower round connection disk;
   (d) the light handle cover comprising a generally hollow cylindrical grip part with a top opening integral with edges of an opening of a protective flange that extends outward from the top opening of the grip part to define a concave space at an underside of the protective flange, the entire light handle cover consisting of molded polymer and the protective flange being semi-rigid;
   (e) the protective flange having generally an umbrella shape comprising an outer round rising plate that rises from an outer edge to a crest, from the crest descends vertically a support wall, and inward from a bottom of the support wall extends a descending round plate to the top opening of the grip part;
   (f) two or more upper connection tabs extending inward from the support wall and defining undercuts with the descending round plate;
   (g) two or more lower connection tabs extending inward from a top section of an inside surface of the grip part near its top opening; and
   (h) the grasping portion is removably insertable into a cylindrical space defined by the inside surface of the grip part, the lower connection tabs are adapted to slip over an outer edge of the lower connection disk and into the lower connection space, and the upper connection contact is adapted to slip past the upper connection tabs and be captured in the undercuts of the upper connection tabs.

2. The assembly of claim 1 wherein the light handle cover is vacuum formed from a sheet of polymer.

3. The assembly of claim 2 wherein the sheet of polymer is less than 0.025 inches thick.

4. The assembly of claim 3 wherein the sheet of polymer is less or equal to 0.013 inches thick.

5. The assembly of claim 2 wherein the sheet of polymer is between 0.010 and 0.015 inches thick.

6. The assembly of claim 1 wherein a wall thickness of the grip part is sufficiently thin so that it has the performance of a grip part of a flexible light handle cover.

7. The assembly of claim 1 wherein a wall thickness of the grip part is 0.002 to 0.008 inches.

8. The assembly of claim 7 wherein a general wall thickness of the protective flange is from 0.010 to 0.015 inches.

9. The assembly of claim 1 wherein the upper connection plate is optionally removable from fixed connection with the rigid light handle.

10. The assembly of claim 1 wherein the upper connection plate and lower connection disk are formed integrally together to form a retrofit part and are joined by a spacer section.

11. The assembly of claim 10 wherein the retrofit part is optionally removable from fixed connection with the rigid light handle.

12. The assembly of claim 10 wherein the retrofit part is adapted to be removably fixed to a rigid light handle which has been separately purchased from the light handle cover and the retrofixed part.

13. The assembly of claim 1 wherein the grip part is a tapered hollow cylinder, with a narrower section toward a lower section of the grip part and with a wider section toward an upper section of the grip part.

14. The assembly of claim 13 wherein a lower end of the grasping portion of the rigid light handle is from 0.125 to 0.750 inches greater in a first horizontal diameter than a second horizontal diameter of the greater part of said grasping portion and the grip part has an internal diameter of from slightly less than the first horizontal diameter to slightly greater than the second horizontal diameter.

15. The assembly of claim 14 wherein the narrower section of the grip part is adapted to remain frictionally in contact with a lower portion of the grasping portion of the rigid light handle when the protective flange is disengaged from the upper connection plate and lower connection space and pulled downward, resulting in inversion of the grip part and capturing of contaminants on an outside surface of the grip part.

16. The assembly of claim 1 wherein an upper surface of the protection flange has lower impressions extending radially outward from the top opening of the grip part and upon the descending round plate and terminate at the support wall.

17. The assembly of claim 16 wherein the upper surface of the protection flange has upper impressions extending radially outward from the crest and across the round rising plate.

18. The assembly of claim 17 wherein the lower impressions and upper impressions are structurally integral with each other and form aligned pairs upon the round rising plate and the descending round plate.

19. The assembly of claim 18 wherein the aligned pairs of lower impressions and upper impressions form a generally oval shape.

* * * * *